(12) United States Patent
Cliff et al.

(10) Patent No.: US 6,885,304 B2
(45) Date of Patent: Apr. 26, 2005

(54) MONITORING OF CROWD RESPONSE TO PERFORMANCES

(75) Inventors: David Trevor Cliff, Bristol (GB); Timothy Alan Heath Wilkinson, Bristol (GB)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/206,832

(22) Filed: Jul. 29, 2002

(65) Prior Publication Data

US 2003/0033600 A1 Feb. 13, 2003

(30) Foreign Application Priority Data

Jul. 27, 2001 (GB) .............................................. 0118452

(51) Int. Cl.⁷ .............................................. G08B 23/00
(52) U.S. Cl. ..................... 340/573.1; 340/589; 340/5.5; 340/500; 340/504; 463/31; 463/32; 463/36; 463/37; 463/43
(58) Field of Search ............................. 340/573.1, 589, 340/5.5, 500, 504; 463/31, 36, 32, 37, 43

(56) References Cited

U.S. PATENT DOCUMENTS

| | | | | |
|---|---|---|---|---|
| 4,739,400 A | * | 4/1988 | Veitch | 84/644 |
| 5,310,962 A | * | 5/1994 | Kimpara et al. | 84/600 |
| 5,436,444 A | * | 7/1995 | Rawson | 250/227.14 |
| 5,629,981 A | | 5/1997 | Nerlikar | 380/25 |
| 6,320,112 B1 | * | 11/2001 | Lotze | 84/615 |

FOREIGN PATENT DOCUMENTS

| | | |
|---|---|---|
| EP | 0 685 825 A2 | 12/1995 |
| EP | 0843432 A2 | 5/1998 |
| EP | 0 893 760 A2 | 1/1999 |
| EP | 1130570 A2 | 9/2001 |
| GB | 2 269 670 A | 2/1994 ......... G01H/13/00 |
| WO | 97/40745 | 11/1997 |
| WO | WO 01/39103 | 5/2001 |

OTHER PUBLICATIONS

WPI Abstract, "*Public Performance Evaluation System,*" Publication No. JP2001–266148 A, Published Sep. 28, 2001.
WPI Abstract, "*Human Reaction Recognizing Device and Computer—Readable Recording Medium Where Program for the Same is Recorded,*" Publication No. JP201–067482 A, Published Mar. 16, 2001.

* cited by examiner

*Primary Examiner*—Daniel J. Wu
*Assistant Examiner*—Tai T. Nguyen
(74) *Attorney, Agent, or Firm*—Lowe Hauptman Gilman & Berner, LLP (57) ABSTRACT

Monitoring apparatus and methods for monitoring the reaction of people to a performance use two or more monitoring devices of different types. Output signals from the monitoring devices are combined to produce at least one crowd reaction signal indicative of the reaction of those people to the performance. Particularly appropriate types of monitoring device are described, as is automatic performance generating apparatus, such an automatic DJ, adapted to use crowd reaction signals to modify performances.

33 Claims, 3 Drawing Sheets

MONITORING OF CROWD RESPONSE TO PERFORMANCES

BACKGROUND OF INVENTION

1. Field of Invention

This invention relates to method and apparatus for monitoring the reaction of people to a performance, and also to apparatus for producing performances modified in response to user reactions. Embodiments are particularly relevant to monitoring the reaction of at least a portion of a crowd to a selection of played songs at an event, and to an automatic disk jockey (DJ) which controls the playing of music at an event in response to the reaction of a crowd.

2. Description of Related Art

While the present invention is relevant to monitoring of various types of performance, it has particular relevance to reactions to and automatic generation of dance music. Terms relevant to dance music will therefore be used here—to help the reader to interpret this text, it is to be understood that the term "song" is intended to cover any piece of music that may or may not include a vocal element. It in particular covers dance music which is best characterised by a repetitive beat, but also covers other types of music including rock and pop music. An individual song is referred to hereinafter as a "track", whilst a selection of individual songs played one after another in a continuous sequence is referred to as a "mix". The term "event" used herein may comprise a dance held in a nightclub or at a private party or social function, or perhaps an outdoor event such as a garden party or festival.

The dance culture is increasing in popularity both in the United Kingdom and overseas. Perhaps the most important element in the success of the dance culture is the DJ—the person who selects the tracks, and the order in which the tracks are played in the mix. In some case the DJ's are becoming as famous as the recording artists themselves. Nightclubs often establish their reputations on the basis of the choice of DJ, and popular DJs often have their own devout following of loyal supporters.

The DJ builds his or her reputation both on their musical taste and as importantly on their ability to change the tracks they are playing in response to the reaction of the crowd. For instance, if a fast tempo record is played and the crowd react favourably the DJ may follow the track with another fast tempo track. If a slow tempo track is played and the DJ sees that a large number of members of the crowd leave the dance floor then the DJ may return to playing fast tempo tracks. Of course, this is a very simplistic view and the DJ needs to rely on an innate ability both to monitor the behaviour of the crowd in order to react to their demand but also to select tracks which directly influence the behaviour of the crowd.

As the importance of the DJ increases, there has been an increasing demand on the owners of clubs to pay for the best DJs to attract the greatest audiences. Whilst this is feasible for the most popular nights—such as Friday or Saturday—the salaries commanded by the best DJs mean that it is often unprofitable to provide the best DJs on other nights where the number of guests will be lower.

At present there is no realistic alternative to the DJ other than the use of pre-recorded selections of tracks. These have the disadvantage that the set of tracks and the order cannot be altered to react to the behaviour of the dancers.

BRIEF SUMMARY OF INVENTION

In accordance with a first aspect the invention provides Monitoring apparatus for monitoring the reaction of people to a performance, the apparatus comprising: two or more monitoring devices each adapted to provide at least one output signal from which the behaviour of at least a portion of those people reacting to the performance can be estimated, wherein the two or more monitoring devices comprise at least one device of a first type and at least one device of a second type, wherein devices of the first type monitor a different quality of user response to devices of the second type; and a processor adapted to process the or each output signal provided by the two or more monitoring devices to produce at least one crowd reaction signal indicative of the reaction of those people to the performance.

The performance may comprise an event such as an indoor dance held in a nightclub or at a private party or event, or perhaps an outdoor event.

The applicant has appreciated that to successfully automate the selection of songs played at an event the behaviour of the crowd must be monitored. This is traditionally the role of a human DJ. The present invention at least partially replaces the DJ by providing a monitoring apparatus that automatically monitors the behaviour of at least a part of the crowd using information obtained at the event.

In accordance with a second aspect the invention provides a method of monitoring the reaction of people at a performance, the method comprising: providing two or more monitoring devices each adapted to provide at least one output signal from which the behaviour of at least a portion of those people reacting to the performance can be estimated, wherein the two or more monitoring devices comprise at least one device of a first type and at least one device of a second type, wherein devices of the first type monitor a different quality of user response to devices of the second type; the monitoring devices of the first type providing a first type of output signal and the monitoring devices of the second type providing a second type of output signal; and processing the output signals to produce at least one crowd reaction signal indicative of the reaction of at least part of the crowd to the performance.

In accordance with a third aspect of the invention, there is provided monitoring apparatus for monitoring the reaction of people to a performance, the apparatus comprising: one or more first monitoring devices each adapted to provide at least one output signal from which the behaviour of an individual reacting to the performance can be estimated; one or more second monitoring devices each adapted to provide at least one output signal from which the behaviour of a plurality of those people reacting to the performance can be estimated; and a processor adapted to process the or each output signal provided by the two or more monitoring devices to produce at least one crowd reaction signal indicative of the reaction of those people to the performance.

In accordance with a fourth aspect of the invention, there is provided a method of monitoring the reaction of people at a performance, the method comprising: providing one or more first monitoring devices each adapted to provide at least one output signal from which the behaviour of an individual reacting to the performance can be estimated and one or more second monitoring devices each adapted to provide at least one output signal from which the behaviour of a plurality of those people reacting to the performance can be estimated; the one or more first monitoring devices and the one or more second monitoring devices providing output signals; and processing the output signals to produce at least one crowd reaction signal indicative of the reaction of at least part of the crowd to the performance.

In accordance with a fifth aspect of the invention there is provided a performance generator for automatically controlling one or more features of a performance, comprising: a memory containing a plurality of performance elements; a processor adapted to receive one or more crowd reaction signals indicative of a reaction of one or more people reacting to the performance, to select one or more performance elements from the plurality of performance elements in response to the one or more crowd reaction signals, and to perform the selected performance elements.

Such a performance generator can be used as automatic DJ apparatus. By choosing which song to play in response to the crowd reaction, the mix can automatically be tailored in order to follow the wishes of the crowd. The DJ apparatus can be used to replace the human DJ at an event.

In a sixth aspect the invention provides a performance generating system for automatically controlling one or more features of a performance in response to user feedback, comprising: one or more monitoring devices each adapted to provide at least one output signal from which the behaviour of one or more of those people reacting to the performance can be estimated; a memory containing a plurality of performance elements; and one or more processors together adapted to process the or each output signal provided by the two or more monitoring devices to produce at least one crowd reaction signal indicative of the reaction of those people to the performance and from the one or more crowd reaction signals to select one or more performance elements from the plurality of performance elements in response to the one or more crowd reaction signals, and to perform the selected performance elements.

In a seventh aspect the invention provides a monitoring device adapted to sense people on a dance floor, comprising a dance floor sensor and adapted to provide at least one output signal from which at least one aspect of the behaviour of at least a portion of those people present at an event can be estimated.

In an eighth aspect the invention provides a data carrier adapted to program the processor of a computing device to control one or more features of a performance in response to user feedback, the programmed processor being adapted to: receive one or more crowd reaction signals indicative of the reaction of people to a performance; from the one or more crowd reaction signals, select one or more performance elements from a plurality of stored performance elements in response to the one or more crowd reaction signals; and perform the selected performance elements.

In a ninth aspect the invention provides a data carrier having stored thereon an output of a performance, wherein said output comprises the performance of selected performance elements from a plurality of performance elements by a programmed processor in response to one or more crowd reaction signals indicative of the reaction of people to a performance.

BRIEF DESCRIPTION OF THE DRAWINGS

There will now be described, by way of example only, one embodiment of the present invention with reference to the accompanying drawings of which.

DETAILED DESCRIPTION OF THE INVENTION

Embodiments will now be described of portable devices for monitoring audience member reactions to performances, of monitoring systems for receiving audience reactions both directly (from, for example, interactively through such portable devices) and indirectly (by monitoring of the environment, or by monitoring parameters of individual or multiple audience members), and of automatic performance generating apparatus (specifically automatic DJ apparatus) using the results of such monitoring. Although the embodiments here are focussed upon dance music and the role of the DJ, it will be appreciated that the principles described here can readily be employed in connection with other types of performance.

Figure 1:
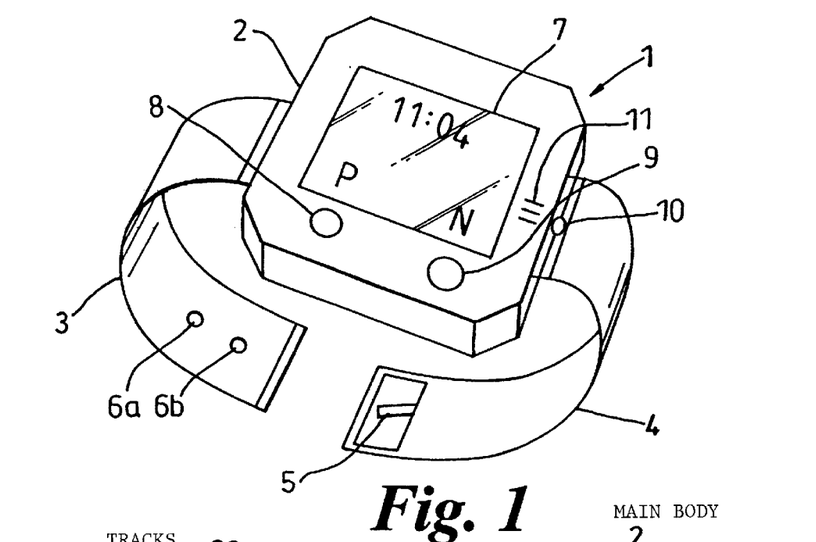
FIG. 1 is a perspective view of a portable device for obtaining reactions of an individual audience member to a performance.

The portable device 1 illustrated in FIG. 1 of the accompanying drawings comprises a main body 2 that is generally rectangular. Two halves 3,4 of a strap extend from opposing sides of the main body 2. One half of the strap is provided with a buckle 5 whilst the other half includes a series of holes 6a, 6b that pass through the strap. The buckle 5 permits the two halves of the strap 3,4 to be securely joined so that the device can be strapped to the wrist of a user. In an alternative construction not shown in the drawings, the main body may be supported by a length of chain which permits it to be worn around the neck of a user.

The main body 2 carries on its front face a display panel 7 which comprises a rectangular liquid crystal display panel. The panel comprises a matrix of liquid crystal elements which can be selectively controlled to display a range of alphanumeric characters on the display. It is also configured to display a range of predefined icons (not shown). It may be backlit for use in low levels of ambient light.

The device 1 can be used to provide a direct audience member response to the music currently or recently playing. Alongside the display panel 7 the main body carries two input buttons 8,9 (an alternative would be for display panel 7 to be touch-sensitive, and for buttons 8,9 or similar inputs to be provided as virtual buttons through the display panel in known fashion for touch-sensitive displays). The buttons 8,9 can individually be operated by the user to input a response to the device 1. In use, the display 7 prompts the user for an input and displays the function of each button. Changing the display permits the function of each button to be varied. The display 7 tells the user the function of each button at any moment in time. A shown in FIG. 1, the display shows a letter "P" next to a first one of the buttons and a letter "N" next to the other. This indicates the user should press the first button 8 if they are enjoying an event (positive reaction) and the second button 9 if they dislike the event (negative reaction). The exact letter or words displayed for a given function will depend to a large extent on the target audience of users for the device.

As well as or in an alternative to a simple button, an input device may be provided which can be set to any one of a range of positions by the user, each position corresponding to a different reaction of the user. For instance, a rotary dial or linear slider may be provided. The position of the dial or slider at one extreme of its range of positions may correspond to most positive (very happy). As the dial or slider is moved to the other extreme of its range of positions it may move through slightly positive (less happy) to slightly negative reaction (unhappy) and at the other extreme indicate a very negative reaction (very unhappy) of the user.

A positive reaction is indicative that the user is enjoying the song and a negative reaction indicates that they dislike the song. Of course, the reaction is relative and it may be that a user experiences a negative reaction to their favourite song simply because it is played at the wrong time at the event or because they are not in the mood to listen to that song.

The display 7 also shows contextual information to the user. As shown in FIG. 1 the device is telling the user the time in the top half of the display 7 and so functions as a wristwatch. A button 10 on the side of the main body allows the user to adjust the settings of the device.

The display may prompt the user to input information using the or each input device. This allows the function of an input device to be varied, with the display telling the user the function of the input device at any given instant. For example, the display may prompt the user to press a particular button if they like a song, or to press it twice in succession if they want to hear a faster song or press a different button to hear a slower song. Later in an event, the display may prompt the user to press the button twice for a slower song, thus altering its use. Such change in function can be triggered by the DJ, for example, if the device 1 contains not only a transmitter but also a receiver that allows it to receive instructions as well as provide user reaction signals.

Device 1 need not be specially constructed for use as a monitoring device. A particularly effective solution may be to program an existing handheld computing device, such as a handheld personal computer, a personal digital assistant (PDA) or a cellular telephone. In such cases, the user interface choices will be those appopriate to the computing device concerned—for a PDA, for example, which will normally have a touch-sensitve screen, it may be advantageous to use virtual buttons of the kind described above.

A direct user response to the performance can thus be provided through the user interface of device 1. However, device 1 can also be used to provide an indirect user response by monitoring the users state of well being or physical behaviour. Device 1 therefore further comprises one or more sensors which each sense a parameter of the users state of well being or physical behaviour, the parameter being indicative of the reaction of the user to a song.

The main body of the device also includes a small microphone 11.1 (shown in FIG. 1) which receives acoustic signals through a small grille opening 11 in the front face of the main body 2. This microphone can therefore sense sounds provided by the user. This microphone can be used for direct user input (essentially a speech user interface for device 1) but can also be used for indirect user input—detecting particular sounds, or words, produced by the user or in his or her vicinity.

Where speech is to be evaluated the device 1 should include a voice-recognition circuit. This may, for example, be adapted to detect one or more keywords spoken by the user. A negative response signal may be produced for one keyword and a positive signal for a different keyword. The voice recognition circuit may be trained to identify the user's voice and may have stored in memory examples of the or each keyword as spoken by the user. These may be entered into the memory in a training mode before the device can be used. The voice recognition circuit then looks for the presence of parts of the signal produced by the microphone which match the keywords stored in memory. Voice recognition is already known in the art and the reader is directed to the teachings of the voice recognition circuit used in prior art mobile phones as an example of the implementation of such a circuit. Voice recognition is of course implementable in software once the voice has been translated into an appropriate digital signal.

A number of sensors (not visible) are also fitted to an under side of the main body 2 in contact with the skin of the user. Where the device 1 is a programmed computing device, these may, for example, communicate with the device 1 in accordance with its normal arrangements for use of peripheral devices. Specific types of sensor device and their significance are described below.

A temperature sensor may be included—if an audience member is dancing enthusiastically, their temperature is likely to be raised.

A perspiration sensor sensitive to the conductivity of an area or point on the users skin may be included. This can provide an indication of how hard the user is perspiring. A heavy rate of perspiration may be used to indicate vigorous dancing indicative of a positive response to a song.

A pulse rate sensor may also be included—again, a high pulse rate is likely to indicate energetic dancing and a positive reaction.

It will be appreciated that monitoring of these features can also in appropriate arrangements allow central determination of whether audience members are at risk of endangering their health (dangerously high temperatures or pulse rates). There are thus reasons to make such sensor results centrally available in the reaction signal provided from device 1 (to provide information centrally that may safeguard user health) but also not to make such sensor results centrally available (protecting the privacy of individual users).

Another sensor that may be used is an inclinometer or an accelerometer which is adapted to produce an output indicative of movement of the portable device. The movement of the device can be used to measure the reaction of the user. If the user is dancing vigorously the device will move around a lot which will indicate the user is reacting positively to a song. If the user is still the output may be interpreted as indicating that the user is reacting in a less positive way to a song.

The device 1 contains a microprocessor and a memory. The microprocessor receives the user reaction signals (whether from the user interface or from sensors) and provide a user reaction signal or signals as output. The microprocessor has access to an area of memory where program instructions and data are stored.

As discussed above, the output signal may contain sufficient information for the value of each reaction signal to be extracted. Thus, the reading of a pulse sensor and the reading of a temperature sensor may be individually extracted from the output signal.

Alternatively, the processor may be adapted to combine one or more reaction signals to produce a combined output signal from which the individual values of the reaction signals cannot be extracted. The combined output signal may encode a single overall reaction value, which may be equal to an average reaction of the user when considering the average of the reaction signals. The combined reaction value may be displayed on the display of the portable device if a display is provided. The user may indicate whether or not they agree with the displayed value.

The amount of processing performed by the processor to produce the output signal will vary from application to application and will depend on the amount of postprocessing that is performed by any central device to which the output signal is transmitted and on the type of monitoring included in the device.

If a number of sensors are provided, the processor may apply a set of logical rules to the output of each sensor in order to provide an overall reaction measurement that can be encoded in the output signal.

For instance, if an inclinometer or accelerometer is provided it may produce an output signal indicating that the user is not moving. If no other sensors or inputs are available this may be interpreted as representing a negative reaction of the user (they are not dancing so probably dislike a song). If, on the other hand, an input device is operated by the user and produces an output indicating that the user likes the song then the output of the accelerometer may be overridden and ignored. The user may simply be tired or just standing still while listening to the song.

The logical rules may define the way in which the reaction signals provided are combined, and which take preference over others.

Figure 2:
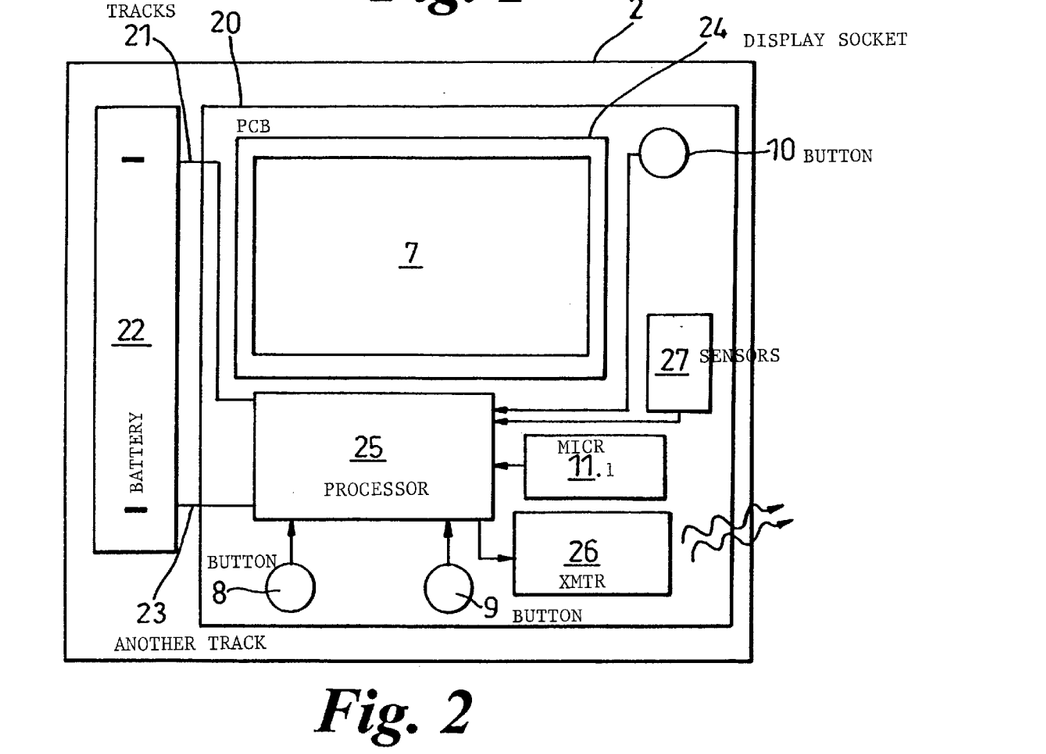
FIG. 2 is a schematic illustration of the functional components of the device of FIG. 1.

FIG. 2 of the accompanying drawings is a schematic illustration of the circuitry and components located within the main body of the device illustrated in FIG. 1 of the accompanying drawings.

The main body 2 houses a printed circuit board 20 which carries tracks defining an electronic circuit. One of the tracks 21 is connected to the positive side of a battery 22 whilst another track 23 is connected to the negative side of the battery 22. This provides the power that is drawn by the circuitry.

The buttons 8,9,10 on the main body 2 are also connected to tracks on the circuit board and the display panel 7 is connected to a multi-pin socket 24 which is soldered to one face of the board 20. The sensors (represented by block 27) are also connected to the processor.

The tracks connected to the buttons 8,9,10 are connected to the input terminals of a processor 25. The processor 25 has access to a memory (not shown). An output terminal of the processor is connected through additional tracks on the circuit board 20 to a display driver device (not shown) which is in turn connected to the display socket 24. Another output from the processor is connected to a wireless radio transmitter 26. The transmitter 26 sends encoded signals from the device to a remote device located at the event. The processor encodes the transmitted signal with information obtained by the sensors and the buttons. An identification code to identify the originating device 1 may also be included. The transmitter may use any appropriate technology—radio-frequency communication is a particularly appropriate technology, and infra-red communication is a possible alternative.

Different approaches may be adopted to providing information from audience members. The device 1 may continuously transmit a current reaction signal, or may transmit a signal at spaced time intervals. For example, a signal may be transmitted as a packet of encoded data at 1 second, or perhaps 1 minute or perhaps 5-minute intervals.

In an alternative arrangement, the portable device may only transmit a signal to the remote apparatus in response to a request from the remote apparatus. This helps to preserve the battery life of the portable device. It also allows a user to wear or carry the device at all times, signals only being transmitted when it is used at an event where an appropriate remote device is located. A further advantage of this mode of operation is that the user does not need to remember to switch the device on at the start of an event and off again at the end of the event.

The memory may also be used to store the response of the user between the transmission of signals to the remote device. The stored responses may be displayed by the user on an appropriate display provided on the portable device.

The output signal sent to the remote device may encode the response of the user in a number of ways. In one arrangement, the signal may encode a simple digital or analogue response value which may vary between an upper and a lower limit, one of the limits indicating a positive reaction and the other a negative reaction. The value may vary linearly between the extremes of the range to indicate any degree of reaction between very positive and very negative.

A positive reaction is indicative that the audience member is enjoying the song or mix of songs played at the event and a negative reaction indicates that he or she dislikes the song or mix of songs. Of course, the reaction is relative and it may be that an audience member (or as will be discussed below, a crowd) experiences a negative reaction to their favourite song simply because it is played at the wrong time at the event or because they are not in the mood to listen to that song. The reaction may indicate the member's preferences for the choice of songs subsequently to be played at the event. A positive reaction may also indicate that a person at the event likes the change from one song to the next at the event.

In a further refinement it is envisaged that the user may operate an input device, such as button, to indicate that they want to "bookmark" a song that is playing, the portable device storing in memory data representing a feature of the song. This may comprise a short recording of the song obtained by a microphone built into the device, or a time-stamp which allows the user to identify the song at a later time from a playlist of the event.

Figure 3:
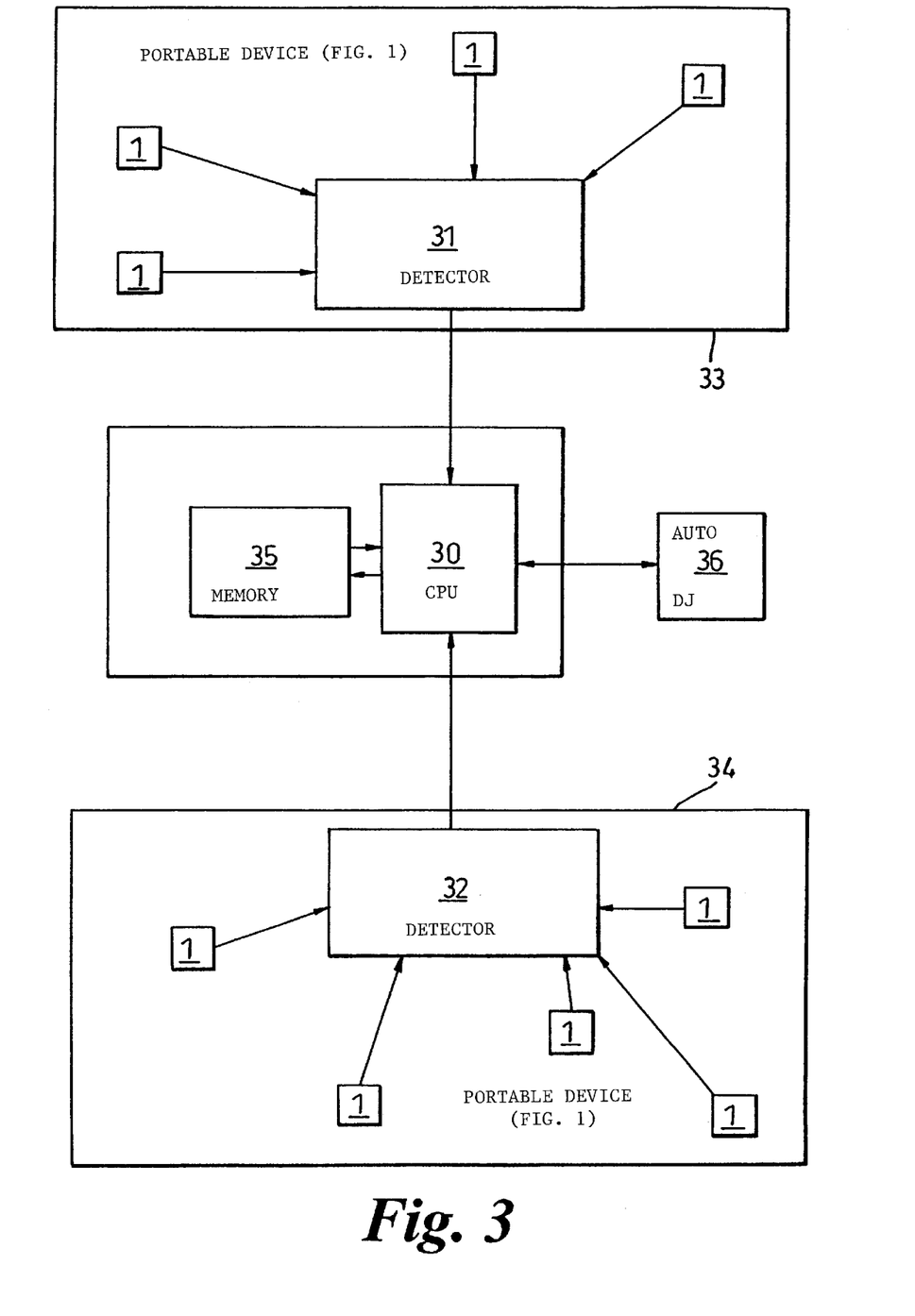
FIG. 3 is a schematic overview of a monitoring apparatus installed at an event which includes a remote device that receives signals from the portable device of FIG. 1.

The portable device 1 is intended to be used in combination with a remote detection apparatus located at the event. FIG. 3 of the accompanying drawings illustrates schematically a simple system suitable for installation in a night club which hosts a dance event. The remote apparatus comprises a central processing unit 30 which will usually be fixed on site and provided by the host of the event or the DJ to help gather information from people at the event. Connected to the central processing unit by electrical cables are two remote devices 31,32 which monitor and detect signals transmitted by portable devices 1 within the club. In fact, the monitoring apparatus receives signals from every device present at the event.

Each detection unit 31,32 comprises a radio frequency detector which detects the signal emitted by any portable devices 1 within its detection range. An amplifier increases the amplitude of the detected signals and 30 passes the signals to a processor. The processor extracts the information encoded in each signal and produces an output signal which is passed down the electrical cable to the main processing unit 30.

One of the remote devices 31 is located in a part of the nightclub containing a dance floor 33 within range of any portable devices worn by users on the dance floor. The other device 32 is located in a different area of the nightclub, such as in a "chill-out" room or eating area 34. This device only detects signals from portable devices worn by occupants of the room.

The main processing unit 30 receives signals along the two cables from each of the detectors 31,32. The signals provide the processor with information about the location of the wearer of a portable device and also the reaction of the wearer to the music that is played. The amount and type of data received depends on the content of the signals transmitted by the portable devices. It is envisaged that some devices may transmit more types of information than others, i.e. some may have increased functionality compared with other devices.

The device 1 may be adapted to receive, as well as to transmit, information. The device 1 may also include a detector which is adapted to receive a signal transmitted by a remote device. The information encoded in the signal may be processed by the processor. It may be used to change the function of any input devices on the portable device, or to display messages or instructions on the display (where provided).

The remote device could, for example, send a request by a DJ or club owner to each or an individual portable device to ask the user for a specific reaction to a song. For example, the user may be asked if the tempo of the song playing is too fast or too slow, or if the music is too loud or quite. This provides a full interaction between the DJ and a user of a portable device.

A display may be provided at the event upon which information can be presented by the user of the portable device. A DJ could, for example, ask the user a question such as "Do you like this song?" The reaction of the user to the question can then be monitored.

The portable apparatus thus monitors the reaction of the user and transmits a signal to a remote device which can be adapted to select the next or any other subsequent track to be played in dependence upon the users response. This allows the user to interact with the tracks played and influence the course of the event.

The data received by the processing unit 30 is stored in a memory 35 and can subsequently be used to produce a control signal which is used either by a human DJ or an automatic DJ apparatus 36 to influence the next or subsequent tracks that are played at the event. For example, if a number of signals are received from portable devices asking for the track to be changed then the track may be changed by the DJ before it would normally end. If a large number of requests for a faster tempo track are received then the music may be changed accordingly.

By choosing which song to play in response to the crowd reaction, the mix can automatically be tailored in order to follow the wishes of the crowd. In effect, control of the mix is at least partially handed over to the people in the crowd and it is the reaction of the crowd that determines which tracks are played. Every event may therefore be unique to the crowd's preferences.

Such monitoring apparatus can thus be used as a tool to assist a DJ by selecting tracks from the memory but leaving the DJ to confirm whether or not to play the selected track. For instance, this gives the DJ extra feedback about the crowd reaction and can assist both skilled and inexperienced DJs alike in pleasing the crowd. However, this type of monitoring apparatus is especially useful in providing a quantified audience reaction to an automatic DJ adapted to reproduce the function of a human DJ.

Figure 4:
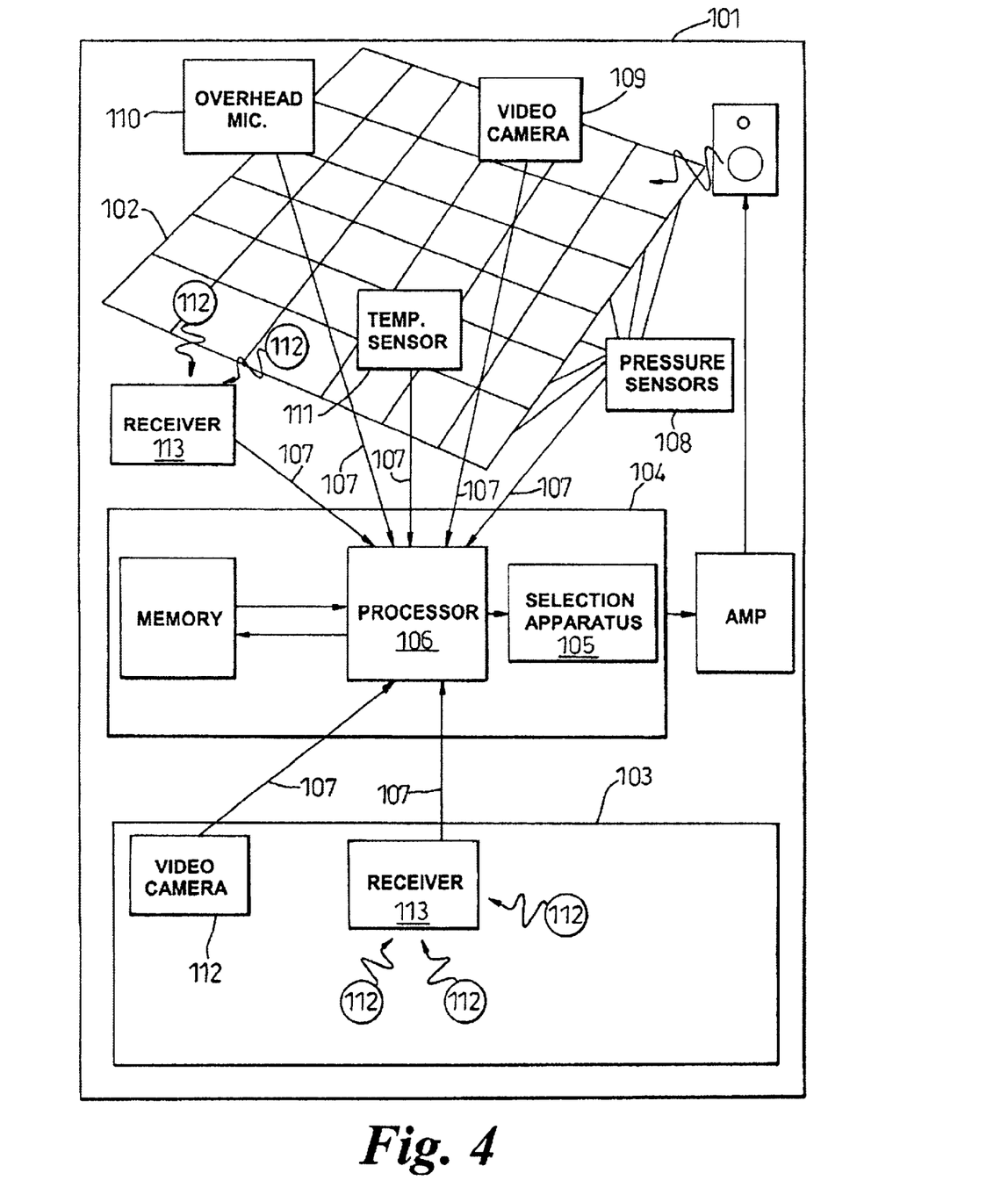
FIG. 4 is a schematic overview a monitoring apparatus according to an embodiment of the invention and used to provide input to an automatic DJ apparatus.

The apparatus illustrated in FIG. 4 shows the integration of user devices as shown in FIGS. 1 and 2 with environmental monitoring to provide a comprehensive monitoring system according to an embodiment of the invention used to provide user input to an automatic DJ system. The system is installed in a hypothetical small nightclub 101 having a single dance floor 102 and a chill-out room/bar area 103. The apparatus monitors the reaction of people in the club to the songs that are being played. It automatically selects songs to be played in response to the monitored reactions of the people, replacing the traditional human DJ at the club.

The apparatus comprises a centrally located automatic DJ 104 which is partially housed within a secure booth adjacent the dance floor 102 inside the nightclub 101. The automatic DJ 104 comprises a selection apparatus 105 and a monitoring apparatus (part of which is housed in the booth). The selection apparatus 105 selects the songs, which are played in response to crowd reaction signals supplied to the selection apparatus by the monitoring apparatus.

The monitoring apparatus comprises a centrally located processing unit 106 located within the secure booth. This may be provided by a microprocessor, which forms a part of a personal computer, or may be a dedicated processing device. The monitoring apparatus is here shown as separate from the automatic DJ 104, but it will be appreciated that these can be integrated together, and may operate under the control of a common processor.

Connected to the processing unit 106 by electrical cables 107 are a range of sensing devices which are spaced around the nightclub. If preferred, a wireless link may be provided between each sensing device and the processor.

Many differing types of sensing device can be employed, as there are many types of behaviour which may be monitored to indicate the reaction of a crowd. These may include, but are not limited to:

Sensors that monitor the number of people dancing to a song,

Sensors that monitor the number of people on a dance floor,

Sensors that monitor the temperature at the event,

Sensors that monitor sound or gestures made by people at the event,

Sensors that directly receive answers to questions asked to people at the event, i.e. "is this too slow/fast, are you tired etc"

The more sensors and the more parameters monitored the more reliable an estimate of the reaction of the crowd to the event can be produced.

Each sensing device produces an electrical output signal which can be used to estimate the reaction of people present in the club to the songs that are being played. These raw output signals are encoded in signals sent along the cables to the central processor. The processor 106 extracts the information encoded in each signal and produces one or more crowd reaction signals.

In the example shown in FIG. 4 several different sensing devices are located in a part of the nightclub containing a dance floor. Other devices are located in a different area of the nightclub, such as in a "chill-out" room or eating area.

Different types of sensing device used or usable in the FIG. 4 embodiment will now be discussed.

A dance floor sensor is adapted to monitor people on a dance floor at the event. Such a dance floor sensor may generate an output signal dependent upon the presence of or the behaviour of the people on the dance floor. One such sensor is the array of independent pressure sensors 108 which may be located on, within or below the surface of the dance floor, covering the whole of or a portion of the dance floor. For example, an array of 6 inch square pressure sensors may be provided which cover an entire area of the dance floor.

The pressure sensors may produce a binary output signal having a first value if a person stands or sits or lies on the sensor and a second value otherwise. Alternatively, the pressure sensors may produce an output signal which indicates the actual pressure applied to a sensor at any time. This permits more sophisticated monitoring.

Where a number of dance floors are provided at an event, such as in a large nightclub, each floor or a subset of the total number of floors may be provided with at least one dance floor sensor.

A digital video camera 109 is adapted to capture a digital image of at least a portion of a dance floor, and has associated with it an image processor adapted to process the digital image to identify the number of people present in the captured image and/or the behaviour of those people. This is preferably a thermal imaging camera but may alternatively or additionally comprise a video camera.

At many events, in order to create the correct ambience the dance floor may be poorly lit. This makes it difficult for a video camera to capture a satisfactory image and also makes it difficult to process the image. A thermal imaging camera may be preferred in such an environment.

The number of people on the dance floor may be estimated from the average temperature of an entire image or by identifying individual people from the features of the image. An estimate based on an average may prove reasonably accurate as the larger the number of people the greater the temperature of the crowd/room is likely to be.

Where a video camera is provided, a laser may be provided which emits a pattern of light towards the dance floor captured in the video image, the image processing means monitoring the pattern of the light from the laser in the image to detect the presence of people in the image.

A microphone 110 or other acoustic sensor is adapted to detect sounds which are produced by people at the event. The sound of the song which is being played at the time of measurement may be subtracted from the output signal from the or each microphone to isolate the sound made from the people at the event from the music.

This sensor may enable production of a crowd reaction signal which has a value dependent upon the amplitude of the sound made by the people in the crowd. For example, the crowd reaction signal may indicate a positive crowd reaction if the crowd are making a lot of noise and a negative reaction if the crowd are silent. The louder the crowd the more positive a crowd reaction signal may be produced.

In a more sophisticated embodiment, the type of sound produced by the crowd may be used to determine the reaction of the crowd. The type of sound may be monitored by appropriate signal processing of the output of the or each or selected ones of the acoustic sensors/microphones.

A crowd reaction signal indicative of a positive crowd reaction may be generated if the output of the microphone has a large high frequency content relative to its low frequency content. This type of sound corresponds to whistling and screaming.

Similarly, a crowd reaction signal indicative of a negative reaction may be generated if the output of the microphone has a small high frequency content relative to its low frequency content. This corresponds to a crowd booing or shouting.

A temperature sensor 111 is adapted to monitor the temperature at the event. The more people who are on a dance floor the higher the temperature. Similarly, the more people enjoy a track the more energetic their dancing will become.

The temperature sensor may, for example, comprise an infrared sensor or a thermal imaging camera. The images captured by a thermal imaging camera may be analysed by an image processor to determine the body temperature of one or more people at an event, and especially of one or more people on a dance floor. Alternatively, as suggested hereinbefore an average temperature for a whole or portion of a captured thermal image may be used.

A crowd reaction signal may be produced which is indicative of a positive crowd reaction if the temperature is increasing or exceeds a predefined threshold, and indicate of a negative reaction if the temperature drops or is below the threshold.

In a sophisticated system, the output of the temperature sensor may be cross-correlated with a measurement of the number of people on the dance floor and/or the type of song that is being played.

A humidity sensor may be provided which is adapted to monitor the amount of moisture in the air. This may be located inside or in front of a duct through which an air conditioning unit extracts air from around a dance floor. It is expected that the humidity will be higher when lots of people are dancing vigorously and this can indicate a positive crowd reaction.

Of course, in other embodiments a smaller range of sensors may be provided whilst in larger nightclubs more sensors may be desirable. A digital video camera 112 is also provided in the chill out room which captures images of the room.

Of course, the presence of a large number of people on a dance floor does not necessarily provide a complete picture of crowd reaction. The behaviour of the people on the dance floor is also an indication of whether or not they are enjoying the event.

The dance floor sensors may be adapted to monitor at least one aspect of the behaviour of the portion of the crowd. This may be adapted to monitor how vigorously the people are dancing by monitoring a pattern of movement of an individual or a crowd.

Where pressure sensors are provided, the rate of change of the output signal from the or each sensor may be used to provided an indication of the movement of the people on the dance floor. For example, if everyone is stood still the sensors will detect the presence of the people but the output of the sensors will remain reasonably constant. If everyone is jumping in time to a track, the output of the sensors will vary in time with the jumping of the crowd.

The variation in the output of the pressure sensors over time may be detected and used. For example, this may be used to distinguish between vigorous dancing and a mass exodus of the dance floor. It is expected that these two different types of movement will have unique time-signature patterns allowing them to be distinguished. A neural network algorithm that is trained to distinguish positive reaction movement patterns from negative patterns of movement may be used in association with main processor 106.

The main processor 106 also receives signals from a number of remote devices which are worn or carried by people 112 in the nightclub. These devices, which may be of the type shown in FIGS. 1 and 2, monitor the users reaction and transmit information wirelessly to receivers 113 located next to the dance floor or a receiver in the chill out room. The receiver sends the received signals back to the processor 106.

The data received by the processor 106 is stored in an area of electrical memory connected to the processor.

The processor produces one or more crowd reaction signals from the information contained in the output signals produced by each of the sensing devices. For the sensors provided in the example, the processor initially generates a crowd reaction signal for each received signal.

Simple examples of logical rules for producing reaction signals that can be applied are as follows:

If the pressure sensors and/or the camera indicate a large number of people are present on the dance floor then the reaction to the currently playing song can be considered positive-they like the song;

If the pressure sensors and/or the camera indicate that a large percentage of the people on the dance floor are dancing then the reaction may be considered to be positive;

If the sensors indicate that the ratio of people on the dance floor to people in the chill-out room is low then the reaction may be considered negative;

If the sensors indicate an increase in the number of people on the dance floor over time then the reaction may be considered positive;

If the sensors indicate a decrease in the number of people on the dance floor over time the reaction may be considered to be negative;

A positive reaction may be generated if the number of people on the dance floor exceeds a predetermined threshold. Conversely, if the number of people falls below the threshold the crowd reaction signal may indicate a negative reaction. The value of the threshold may be varied as a function of a parameter of the event. For instance, if the event is a dance at a nightclub a different threshold may be used for different nights of the week. For regular events, the value of the threshold may be adjusted by monitoring the number of people on the dance floor over a number of events and calculating an average value, the threshold corresponding to the calculated average value. The threshold may also be adjusted as a function of the total number of people at the event.

If the temperature on the dance floor is increasing this may be used to indicate a positive reaction (more heat equals more people or more vigorous dancing).

The value of the crowd reaction signal may be scaled by a scaling factor to take into account parameters such as the time of day, day of the week, or the time since the start of the event. For instance, a greater percentage should be on the dance floor at the middle of an event than at the start of the event. Other context information such as the time of day/night, day of the week etc. can be employed.

Having produced a number of crowd reaction signals, the processor then applies a number of logical rules to the individual crowd reaction signals to produce an overall crowd reaction signal. For example:

If the number of people on the dance floor is high (indicated by the pressure sensors) but they are not moving much (indicated by a low temperature) the reaction is considered slightly positive. If they are moving a lot then a very positive overall reaction signal is generated.

If the number of people on the dance floor is high and they are moving a lot but the crowd reaction signal produced from the output of a microphone is negative (perhaps because the crowd are booing or hissing) then the microphone reaction signal will dominate and a negative overall reaction signal value will be produced.

Having produced an overall crowd reaction signal the processor passes the signal to the selection means. The selection means (most obviously implemented as a processor operating under appropriate program control) is adapted to select a song to play in the nightclub from a large collection of tracks stored in the memory. An index list is also stored in the memory which comprises at least one classification value for each stored track. For instance, the index for a track may indicate the tempo of the track, how the tempo changes during the duration of the track etc.

The selection means may generate a selection value from the one or more control signals and select a track to play from the memory by comparing the selection value with the index for a stored track. For example, the selection value may comprise a tempo value, and a track having an index representing that tempo may be selected. If a number of tracks are stored in memory which match the criteria of the selection value then the track may be selected at random from all the possible matches.

The selection means processes the crowd reaction signal together with historical data corresponding to the current playing song and previously played songs. In this simple example, the historical data indicates the tempo of the current playing song and the tempo of the song prior to it. Logical rules are then applied to the historical data and the crowd reaction signal value to determine the tempo of the next song that should be played.

The logical rules may include the following:

If, when the automatic DJ increases the tempo of the songs by cross-fading to a new song faster than the previous song a positive crowd reaction is identified then the automatic DJ should ensure that the tempo continues to increase by selection of a faster tempo track or stays the same;

If, when the automatic DJ increases the tempo of the songs by cross fading to a new song faster than the previous song a negative crowd reaction is identified then the automatic DJ should ensure that the tempo decreases by selection of a slower tempo track;

If, when the automatic DJ deceases the tempo of the songs by cross-fading to a new song slower than the previous song a positive crowd reaction is identified then the automatic DJ should ensure that the tempo continues to decease by selection of a slower tempo track or stays the same;

If, when the automatic DJ decreases the tempo of the songs by cross-fading to a new song slower than the previous song a negative crowd reaction is identified then the automatic DJ should ensure that the tempo is increased by selection of a faster tempo track.

Having determined the tempo of the next song to play the selection means chooses a song from the memory using the index list to ensure it has the required tempo. If more than one track meets the criteria a track may be picked at random from all the matches.

The selection means also writes to the memory a set of reaction marker values, each value being associated with a played track and indicating whether or not it generated a positive or a negative crowd reaction. When subsequently choosing between tracks that meet the tempo criteria, the track with the most positive reaction marker value associated with it may be selected.

The marker values may be updated each time a track is played and the reaction of the crowd is monitored. For example, the marker value may comprise an average reaction value determined once the track has been played a number of times at an event.

The apparatus may be adapted to delete a track from the memory if the marker value associated with the track is indicative of a very unpopular track. A marker may indicate such a low popularity if it corresponds to a track that has been played a predefined number of times and has a popularity below a predefined threshold.

The selection apparatus may also be arranged to control other aspects of the event such as the volume of the songs that are played and the pattern and intensity of lighting used at the event, smoke machines or foam/bubble generators etc.

The discussion aboves relates essentially to musical performance, but it will be appreciated that other forms of performance can be modified in the same way. For example, visual art can be created according to rules and modified according to user reaction to the current form of the art—this could apply to static or video images.

In a modification (again most obviously applicable to music but potentially applicable to other forms of performance), the remote device may not affect the tracks being played or to be played but instead store the users reactions during at least a portion of the event together with information about the tracks played in that portion of the event. The remote device may select the tracks which generated the most positive reactions from the user, and copy the selected tracks to a storage medium. This medium may be a web page or a compact disc or minidisc. The site can then be viewed by anyone after the event, or the CD may be sold to the crowd at the end of an event.

What is claimed is:

1. Monitoring apparatus for monitoring the reaction of people to a performance, the apparatus comprising:
    two or more monitoring devices, each adapted to provide at least one output signal from which the behaviour of at least a portion of those people reacting to the performance can be estimated, wherein the two or more monitoring devices comprise at least one device of a first type and at least one device of a second type, wherein devices of the first type monitor a different quality of user response to devices of the second type, the device of the first type being a dance floor sensor adapted to monitor people on a dance floor at the performance, the dance floor sensor comprising a thermal imaging camera adapted to capture a digital image of at least a portion of a dance floor, and an image processor adapted to process the image to identify the number of people present in the captured image, the behaviour of those people, or both; and
    a processor adapted to process the at least one output signal provided by the two or more monitoring devices to produce at least one crowd reaction signal indicative of the reaction of those people to the performance.

2. Apparatus according to claim 1, in which the first type of monitoring device is one of the following device types, and the second type of monitoring device is a different one of the following device types:
    monitor for detecting the movement or location of people;
    monitor of ambient temperature;
    monitor for detecting sounds or gestures made by people;
    monitor for providing direct feedback from individuals; and
    monitor of ambient humidity.

3. Apparatus according to claim 1 in which the dance floor sensor comprises one or more pressure sensors located on, within or below the surface of the dance floor.

4. Apparatus according to claim 1, in which the processor is arranged to generate a crowd reaction signal indicative of a positive reaction if the number of people on the dance floor increases and a negative crowd reaction if it decreases.

5. Apparatus according to claim 1, in which the processor is arranged to generate a crowd reaction signal that is indicative of a positive reaction if the number of people on the dance floor exceeds a predetermined threshold.

6. Apparatus according to claim 1, in which the first type of monitoring device is a microphone for monitoring at least a portion of the people reacting to the performance.

7. Apparatus according to claim 6, in which the processor is arranged to produce a crowd reaction signal which has a value dependent upon the amplitude of the sound measured by the microphone.

8. Apparatus according to claim 6, in which the processor is arranged to produce a crowd reaction signal dependent upon the type of sound produced by the crowd.

9. Apparatus according to claim 1, in which the first type of monitoring device is a portable monitoring device worn or carried by at least one person reacting to the performance to provide feedback from the person.

10. Apparatus according to claim 9, in which the feedback is solicited feedback.

11. Apparatus according to claim 10, in which the feedback is personal biometric data.

12. Monitoring apparatus for monitoring the reaction of people to a performance, the apparatus comprising:
    two or more monitoring devices, each adapted to provide at least one output signal from which the behaviour of at least a portion of those people reacting to the performance can be estimated, wherein the two or more monitoring devices comprise at least one device of a first type and at least one device of a second type, wherein devices of the first type monitor a different quality of user response to devices of the second type, the device of the first type being a dance floor sensor adapted to monitor people on a dance floor at the performance;
    a processor adapted to process the at least one output signal provided by the two or more monitoring devices to produce at least one crowd reaction signal indicative of the reaction of those people to the performance; and
    a sensor adapted to monitor people not on a dance floor at the performance, whereby the processor is thereby able to obtain an output signal representative of a percentage of people attending the performance and on the dance floor.

13. Monitoring apparatus for monitoring the reaction of people to a performance, the apparatus comprising:
    one or more first monitoring devices, each adapted to provide at least one output signal from which the behaviour of an individual reacting to the performance can be estimated;
    one or more second monitoring devices, each adapted to provide at least one output signal from which the behaviour of a plurality of those people reacting to the performance can be estimated, at least one of the one or more second monitoring devices being a dance floor sensor adapted to monitor people at the performance, the dance floor sensor comprising a thermal imaging camera adapted to capture a digital image of at least a portion of a dance floor, and an image processor adapted to process the image to identify the number of people present in the captured image, the behaviour of those people, or both; and
    two or more monitoring devices to produce at least one crowd reaction signal indicative of the reaction of those people to the performance.

14. Monitoring apparatus according to claim 13, wherein at least one of the first monitoring devices is a portable monitoring device worn or carried by at least one person at the event to provide feedback from the person.

15. Monitoring apparatus according to claim 14, wherein at least a part of the feedback is arranged to be provided by the person through a user interface.

16. Monitoring apparatus according to claim 14, wherein the portable monitoring device comprises a biometric sensor.

17. Monitoring apparatus according to claim 13, in which the dance floor sensor comprises one or more pressure sensors located on, within or below the surface of the dance floor.

18. Monitoring apparatus according to claim 13, in which at least one of the one or more second monitoring devices is a microphone for monitoring at least a portion of the people reacting to the performance.

19. Monitoring apparatus according to claim 18, in which the processor is arranged to produce a crowd reaction signal dependent upon the type of sound produced by the crowd.

20. Monitoring apparatus for monitoring the reaction of people to a performance, the apparatus comprising:
- one or more first monitoring devices, each adapted to provide at least one output signal from which the behaviour of an individual reacting to the performance can be estimated;
- one or more second monitoring devices, each adapted to provide at least one output signal from which the behaviour of a plurality of those people reacting to the performance can be estimated, at least one of the one or more second monitoring devices being a dance floor sensor adapted to monitor people at the performance, and at least a further one of the one or more second monitoring devices is a sensor adapted to monitor people not on a dance floor at the performance, whereby the processor is thereby able to obtain an output signal representative of a percentage of people attending the performance and on the dance floor; and
- two or more monitoring devices to produce at least one crowd reaction signal indicative of the reaction of those people to the performance.

21. A performance generating system for automatically controlling one or more features of a performance in response to user feedback, comprising:
- one or more monitoring devices, each adapted to provide at least one output signal from which the behaviour of one or more of those people reacting to the performance can be estimated, at least one of the one or more monitoring devices being a dance floor sensor adapted to monitor people on a dance floor at the performance, the dance floor sensor comprising a thermal imaging camera adapted to capture a digital image of at least a portion of a dance floor, and an image processor adapted to process the image to identify the number of people present in the captured image, the behaviour of those people, or both;
- a memory for containing a plurality of performance elements; and
- one or more processors together adapted to process the at least one output signal provided by the one or more monitoring devices to produce at least one crowd reaction signal indicative of the reaction of those people to the performance and from the one or more crowd reaction signals to select one or more performance elements from the plurality of performance elements in response to the one or more crowd reaction signals, and to perform the selected performance elements.

22. A performance generating system according to claim 21, in which at least one of the one or more monitoring devices is a dance floor sensor adapted to monitor people on a dance floor at the performance.

23. A performance generating system according to claim 22, in which the dance floor sensor comprises one or more pressure sensors located on, within or below the surface of the dance floor.

24. A performance generating system according to claim 21, in which at least one or the one or more monitoring devices is a microphone for monitoring at least a portion of the people reacting to the performance.

25. A performance generating system according to claim 21, in which at least one of the one or more monitoring devices is a portable monitoring device worn or carried by at least one person reacting to the performance to provide feedback from the person.

26. A performance generating system according to claim 25, in which the one or more processors are arranged to solicit the feedback.

27. A monitoring device adapted to sense people on a dance floor, comprising a dance floor sensor and adapted to provide at least one output signal from which at least one aspect of behaviour of at least a portion of those people present at an event can be estimated, the dance floor sensor comprising a thermal imaging camera which is adapted to capture a digital image of at least a portion of the dance floor, and an image processor adapted to process the image to identify the number of people present in the captured image or the behaviour of those people or both.

28. A device according to claim 27, in which the dance floor sensor comprises one or more pressure sensors located on, within or below the surface of the dance floor.

29. A device according to claim 27, further comprising a processor and adapted to generate a crowd reaction signal indicative of a positive reaction if the number of people on the dance floor increases and a negative crowd reaction if it decreases.

30. A device according to claim 27, further comprising a processor and adapted to generate a crowd reaction signal that is indicative of a positive reaction if the number of people on the dance floor exceeds a predetermined threshold.

31. A device according to claim 30, in which the value of the threshold is variable as a function of a parameter of the event.

32. A device according to claim 31, in which the threshold is adjustable as a function of the total number of people at the event.

33. A monitoring device adapted to sense people on a dance floor, comprising a dance floor sensor and adapted to provide at least one output signal from which at least one aspect of behaviour of at least a portion of those people present at an event can be estimated; and
- a processor and at least one further sensor for monitoring the number of people present at the event that are not on the dance floor, the processor being arranged to combine output of the further sensor and the dance floor to provide an output signal representative of the percentage of people on the dance floor.

* * * * *